(12) United States Patent
Braun (10) Patent No.: US 8,876,858 B2
(45) Date of Patent: Nov. 4, 2014

(54) SURGICAL INSTRUMENT WITH ELASTICALLY MOVABLE INSTRUMENT HEAD

(75) Inventor: Marcus Braun, Holzgerlingen (DE)

(73) Assignee: Tuebingen Scientific Medical GmbH, Tuebingen (DE)

( * ) Notice: Subject to any disclaimer, the term of this patent is extended or adjusted under 35 U.S.C. 154(b) by 0 days.

(21) Appl. No.: 13/087,238

(22) Filed: Apr. 14, 2011

(65) Prior Publication Data

US 2012/0265176 A1   Oct. 18, 2012

(30) Foreign Application Priority Data

Apr. 14, 2010   (EP) ..................................... 10003949

(51) Int. Cl.
  *A61B 17/00* (2006.01)
  *A61B 17/29* (2006.01)
  *A61B 18/14* (2006.01)

(52) U.S. Cl.
  CPC ......... *A61B 17/29* (2013.01); *A61B 2017/2927* (2013.01); *A61B 2017/00738* (2013.01); *A61B 18/1445* (2013.01); *A61B 2017/2902* (2013.01); *A61B 2017/291* (2013.01); *A61B 2017/2929* (2013.01); *A61B 2017/294* (2013.01)
  USPC .......................................... 606/205; 606/52

(58) Field of Classification Search
  CPC ................... A61B 17/28; A61B 17/29; A61B 2017/2901–2017/2904; A61B 2017/2919; A61B 2017/2926; A61B 2017/2927; A61B 2017/2929
  USPC ......... 606/205–209, 48, 51, 52; 600/139–142
  See application file for complete search history.

(56) References Cited

U.S. PATENT DOCUMENTS

| 1,429,580 | A |   | 9/1922 | Geiger |
|---|---|---|---|---|
| 5,549,637 | A | * | 8/1996 | Crainich ...................... 606/207 |
| 5,906,629 | A | * | 5/1999 | Oren et al. .................... 606/205 |

(Continued)

FOREIGN PATENT DOCUMENTS

| GB | 494057 | 10/1938 |
|---|---|---|
| GB | 2226617 A | 7/1990 |
| WO | WO2009091497 A2 | 7/2009 |

OTHER PUBLICATIONS

European Search Report for EP Patent Application No. 10003919.4, dated Sep. 24, 2010.

*Primary Examiner* — Darwin Erezo
*Assistant Examiner* — Lindsey Bachman
(74) *Attorney, Agent, or Firm* — AlbertDhand LLP (57) ABSTRACT

Disclosed is a surgical instrument comprising an instrument handle, an instrument shaft shaft having a distal end and a proximal end at which the instrument handle is linked, an instrument head, pivotally linked to the distal end of the instrument shaft via a hinge shaft or pins and comprising an effector rotatably supported in said instrument head around its longitudinal axis as well as a surgical tool held by said effector, and a mechanical transmission system at least partially arranged within said instrument shaft transmitting mechanical operation signals from said instrument handle to said instrument head at least for pivoting and/or rotating motions. A bending flexible as well as rotating rigid, hollow spindle is arranged bypassing said hinge shaft or pins and directly connecting said effector with the mechanical transmission system for transmitting at least rotating signals via said spindle to said effector.

4 Claims, 5 Drawing Sheets

(56) References Cited

U.S. PATENT DOCUMENTS

| | | |
|---|---|---|
| 7,544,197 B2 * | 6/2009 | Kelsch et al. ............... 606/129 |
| 7,549,998 B2 * | 6/2009 | Braun ........................ 606/205 |
| 7,674,255 B2 | 3/2010 | Braun |
| 2006/0020241 A1 | 1/2006 | Piskun |
| 2007/0244512 A1 * | 10/2007 | Measamer ................ 606/205 |
| 2008/0188891 A1 | 8/2008 | Frank |
| 2009/0088792 A1 | 4/2009 | Hoell |
| 2011/0068147 A1 * | 3/2011 | Racenet et al. ............ 227/180.1 |

* cited by examiner

SURGICAL INSTRUMENT WITH ELASTICALLY MOVABLE INSTRUMENT HEAD

BACKGROUND OF THE INVENTION

1. Field of the Invention

The present invention relates to a surgical instrument especially for minimally invasive surgery having a distal instrument head moveably connected to an instrument or tube shaft.

2. Discussion of the Prior Art

For example, from DE 100 36 108, a surgical instrument of this kind is known. It substantially consists of a tube or instrument shaft at the one proximal end of which an instrument handle is arranged for the operation of an instrument head disposed at the opposed distal end of the tube shaft via a transmission path. The instrument head can be bent, or rather inclined with respect to the tube shaft and, moreover, holds an effector rotatably supported in the instrument head in the form of a type of forceps or tongs, one jaw of which is pivotably supported on the effector and is likewise operable by means of the instrument handle.

In more concrete terms, the transmission enables at least a first movement of the instrument handle, according to this prior art to be triggered by rotation of an operator's hand, to be transformed into a rotation of the effector at a predetermined transmission ratio with respect to this operating movement. This makes it possible to rotate the effector despite the relatively restricted possibility of motion of a human hand about up to 300°, for instance, and, thus, to realize complex motions without changing the grip at the handle. Moreover, a second movement of the instrument handle, for instance, bending the same with respect to the tube shaft, is converted into an inclination movement of the instrument head.

The transmission provided inside the instrument handle and the tube shaft is designed such that a most largely decoupled operation of each individual movement of the instrument head and the effector is permitted. However, such a transmission is necessarily extremely complex and consequently also requires sufficient assembly space. Moreover, a complete decoupling of the individual movements is not completely ensured.

In WO 2009/001 497 A2 another surgical instrument is disclosed comprising an instrument handle, an instrument shaft having a distal end and a proximal end at which the handle is connected and an instrument head, pivotally linked to the distal end of the instrument shaft. The instrument head comprises an effector rotatably supported in the instrument head around its longitudinal axis as well as a surgical tool held by the effector. A mechanical transmission system is provided at least partially within the instrument shaft transmitting and/or converting mechanical operation signals from the handle to the instrument head at least for pivoting and/or rotating motions. Finally, a bending flexible as well as torsional rigid, hollow spindle is interconnected in the transmission system bypassing the hinge and directly connecting the effector with the mechanical transmission system for transmitting at least rotating signals from the handle to the effector. Here, the bending flexible as well as torsional rigid, hollow spindle is a spiral spring, which is mounted on its one end to an rotating tube shaft at least rotatably supported within the instrument shaft as a member of said transmission system.

In view of this prior art, it is an object of the present invention, to provide a surgical instrument of this generic type in which motions of an instrument head as well as of an effector can be performed using a transmission having a simple design especially in the area of the instrument head. Another target of the invention is, to provide free space especially in the area of the instrument head by simplifying the design of the transmission which space can be used for applying additional functions to the surgical instrument which are useful for surgical treatment. A further target of the invention is to provide a surgical instrument adapted for single port surgery according to the common definition in the field of minimal invasive surgery.

SUMMARY OF THE INVENTION

This object is achieved by a surgical instrument comprising the technical features according to the patent claim 1. Further advantageous configurations of the invention are the subject matter of the dependent claims.

The basic concept of the invention refers to the arrangement of a flexible spindle being torsional rigid so that the spindle is capable of transmitting torque. This spindle forms a member of the transmission between a signal generator giving mechanical signals like an instrument handle having a plurality of triggers, knobs, etc., an robotic interface, or driving motors like cylinders, piezoelectric elements, stepping motors, etc. and an instrument head linked to an instrument shaft via a mechanical hinge (comprising a hinge shaft or pins). Furthermore, the spindle is arranged to bypass the hinge in order to connect an effector supported within the instrument head (directly) with the transmission, especially a rotating (tube) shaft forming another member of the transmission which rotating tube shaft is supported within the instrument shaft to transmit mechanical rotating signals from the signal generator to the effector. This design (especially the combination of the hinge with the flexible spindle) results in a guided (controlled) bending movement of the spindle when the instrument head will be pivoted versus the instrument shaft such that the spindle can be predictably designed for max. torque transfer. Additionally, it will be possible that a change in axial length of the spindle during the bending movement can be minimized and/or accurately predicted.

More concrete, the surgical instrument according to the invention comprises a mechanical signal generator especially an instrument handle, an instrument shaft having a distal end and a proximal end at which the signal generator is linked, an instrument head, pivotally linked to the distal end of the instrument shaft via a hinge shaft or pins and comprising an effector rotatably supported in the instrument head around its longitudinal axis as well as a surgical tool held by the effector, and a mechanical transmission system which is at least partially arranged within the instrument shaft for transmitting mechanical operation signals from the signal generator to the instrument head at least for pivoting and/or rotating motions. According to the invention a bending flexible as well as torsional rigid, hollow spindle is provided bypassing the pivoting hinge and directly connecting the effector with the mechanical transmission system (rotating shaft) for transmitting at least rotating signals via the spindle to the effector. By the bypassing arrangement, which means that the spindle is arranged separately to the hinge, it can be achieved in that the instrument head when pivoting around the fixed hinge axis creates a bending motion of the spindle combined with a compression or bulging action of the spindle.

The bending flexible as well as the torsional rigid, hollow spindle according to the invention is a spiral spring, which is mounted on its one end to a rotating (tube) shaft which is at least rotatably and optionally axially shiftably supported within the instrument shaft as a member of the transmission system. The rotating (tube) shaft has preferably an inner axial bore entering into the hollow spindle to form a closed channel, through which additional elements like push/pull-elements and/or electric wirings can be fed, as will be discussed later. In case the spindle is a spiral spring the above compression action leads to a shortening of its axial length so that the influence of the bending motion to the position of the surgery tool can be reduced.

Finally, according to the invention the pitch of the spring coils is adjusted such that in case the spiral spring is maximally bent in accordance with the maximum pivoting position of the instrument head the spring coils at the inner side of the spring with respect to the bending direction are just in touch with each other or still spaced apart from each other. This inventive design has the advantage in that the spring having a given outer and inner dimension can transmit a maximum value of torque in the max. pivoted position of the instrument head so that the torque transmission capacity of the spiral spring can be optimally used.

According to an aspect of the invention, the surgical tool is a forceps or a scissors means comprising two jaws, respectively, wherein at least one of them is pivotably supported by the effector and linked to the transmission system, especially to an actuating rod inside the rotating tube shaft via a lever means (might be integral with the respective jaw) and connecting elements (for example Bowden cables) such that an axial shift of the actuating rod caused by respective operating signals from the signal generator is directly transmitted via the connecting element(s) and the lever means to the at least one jaw for an opening/closing motion. It shall be noted, that the actuating rod could be an additional (separate) rod shiftably supported in the axial bore of the rotating (tube) shaft or it could be the rotating (tube) shaft itself which shaft would then have two functions, namely the transmission of rotating signals to the effector and the transmission of actuating signals (opening/closing signals) to the surgical working tool.

Another aspect of the invention is directed to the tube or instrument shaft of the surgical instrument which shaft is formed in a single C-shape along its longitudinal direction or comprises a plurality of single curved portions having identical or different radii to each other to simulate a C-shaped curve (in one plane). This shaft design forms the basis to insert a plurality (at least two) of surgical instruments of the invention into a single trocar in case of a so-called single port surgery wherein the signal generators (handles) of each instrument do not interfere each other. Furthermore, the C-shape or C-shape like form has the advantage in that the distal end portions of the instruments are automatically distanced from each other such that there is no need anymore to cross the instruments shafts when passing through the single port trocar to achieve a specific distance between the distal end portions as is the case in the prior art. Additionally, the instruments can be inserted and removed into/out of the trocar separately and individually from each other.

It shall be noted here, that the single curve direction of each instrument shaft is in conformity with the pivoting direction of the instrument head. In other words, in case two surgical instruments having (single) curved instruments shafts as defined above are inserted into one single trocar for single port surgery such that the signal generators (handles) are spaced apart from each other, the instrument heads of both instruments can be pivoted to approach each other again. Therefore, single port surgical treatment can be carried out by providing more working space also by using two instruments in co-operation with each other.

According to another aspect of the invention the spindle (and optionally also the instrument shaft) has an outer diameter of max. 5.5 mm wherein the spindle has an inner diameter of min. 0.3 mm. The inventors found out that a spindle especially in the form of a spiral spring made of a spring material having a tensile strength $Rm \geq 1100$ $N/mm^2$ and having a dimension as defined above is able to transfer a sufficient torque from the rotating (tube) shaft to the effector and parallel thereto being flexible (elastic) enough to be bent when pivoting the instrument head without generating high resisting power. Furthermore, the inner diameter allows the insertion of at least one cable capable of transmitting actuating (shear/pull) forces from the transmission (actuating rod) to the surgical working tool and optionally to feed electric power to the surgical working tool to generate heat according to bipolar technology.

Hereinafter, the invention will be explained in detail by example of a preferred embodiment with reference to the accompanying drawings, in which.

DETAILED DESCRIPTION OF THE PREFERRED EMBODIMENT

Figure 1:
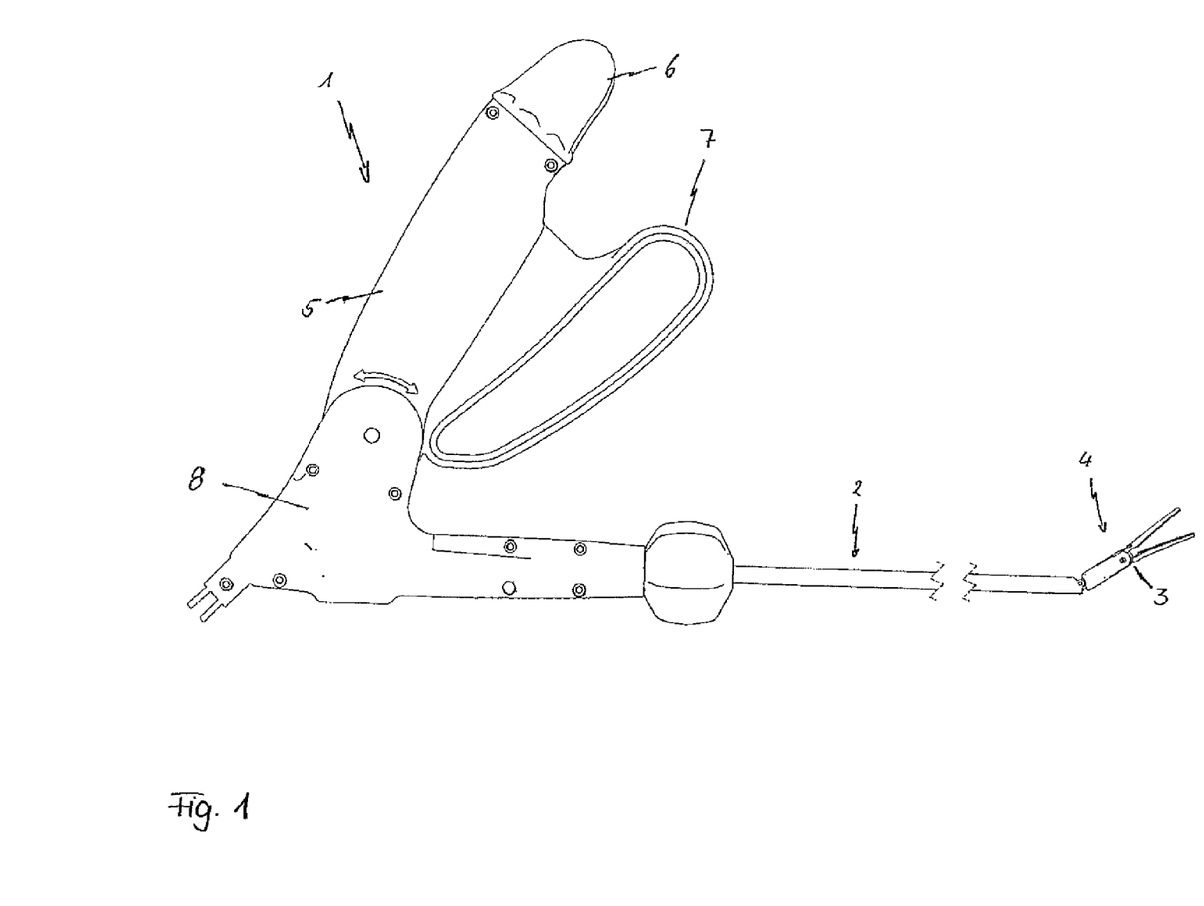
FIG. 1 shows a perspective view of a surgical instrument according to a preferred embodiment of the invention.

In FIG. 1, a complete surgical instrument according to a preferred embodiment of the invention is shown in a perspective view. The surgical instrument according to the invention consequently has a mechanical signal generator in the form of a multi-functional instrument handle 1 which is arranged at a proximal end or end portion of a tube or instrument shaft 2, preferably made of stainless steel, as well as an instrument head 4 equipped or adapted to be equipped with an effector 3, the instrument head being provided at the other, distal end of the instrument shaft 2.

As can be seen from FIG. 1 the tube or instrument shaft 2 can have a C-shaped curve wherein the C-shape is achieved by a single radius or by a plurality of curved portions (having the same curving direction) distanced from each other in the longitudinal direction and having identical or different radii, respectively. Alternatively, the instrument shaft 2 can also have a straight shape or the instrument shaft has at least one straight portion and at least one C-shaped portion just to approach a single curved design.

In general, the instrument head 4 is supported at the respective instrument shaft end such that it can be pivoted or bent with respect to the instrument shaft 2, whereas the effector 3 can be turned or rotated in each bending position of the instrument head 4 about the longitudinal axis of the latter, the two afore-mentioned motions being adapted to be performed by means of the instrument handle 1. To this end, a number of manipulators or operating mechanisms are provided at the instrument handle 1 and are operatively connected, via corresponding transmission trains inside the instrument handle 1 as well as inside the instrument shaft 2, to the instrument head 4 and the effector 3, respectively, so as to be able to perform the individual motions of the instrument head 4 and of the effector 3 independently of each other.

Specifically, the instrument handle 1 consists of an ergonomically shaped handle piece 5 which is mounted in a pivotable and inclinable manner to the instrument shaft 2 and on which a first manipulator 6, preferably in the form of a rotary knob, and a second manipulator 7, preferably in the form of a handle lever or trigger, are supported. Thus, the instrument handle 1 according to the preferred embodiment of the present invention comprises a total of operating mechanisms for three independent movements of the effector 3 and/or the instrument head 4. It is explicitly emphasized in this context that the instrument handle 1 may also have fewer operation possibilities, for instance only one manipulator or operating mechanism, respectively, for pivoting the instrument head 4 and rotating the effector 3.

Figure 2:
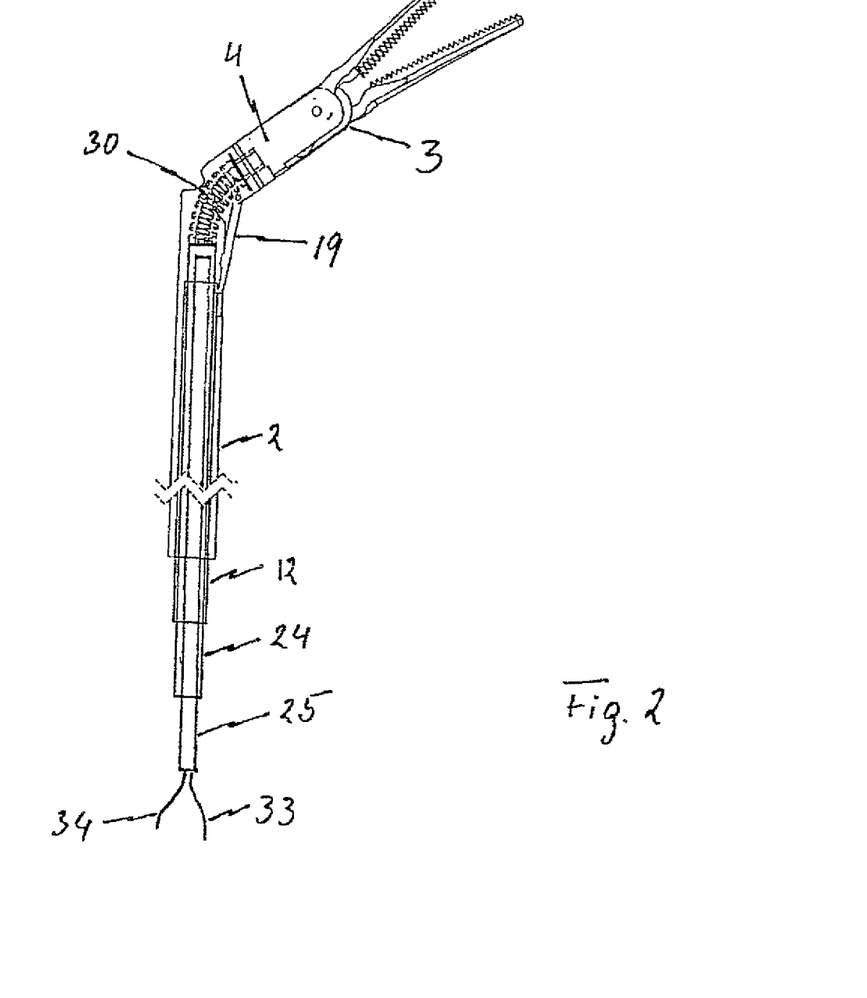
FIG. 2 shows a schematic view of a transmission system for transferring actuating movements of/at an instrument handle to an instrument head for pivoting and/or rotating maneuvers.
Figure 3:
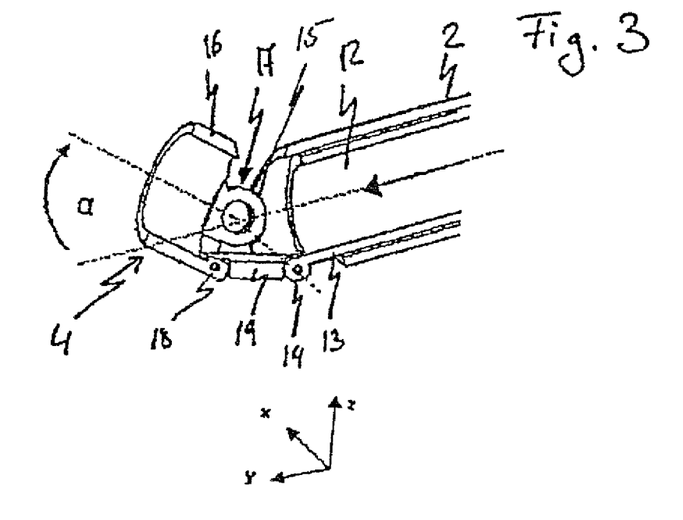
FIG. 3 shows an enlarged view of a hinge portion between the instrument head and an instrument shaft (without the flexible spindle)

The exterior structure of the instrument handle 1, especially with respect to the operating mechanism for pivoting/bending the instrument head 4 and with respect to the corresponding bending transmission train is shown in FIG. 2 and FIG. 3.

The handle 1 schematically shown in FIG. 1 is pivotably connected to the instrument shaft 2 via a coupling member 8 which, in turn, is coupled to an axially shiftable pushing or pivoting (tube) shaft 12 (see FIG. 3) supported inside of the instrument shaft 2. The coupling member 8, therefore, transmits a tilting or pivoting motion of the handle 1 relative to the instrument shaft 2 into a linear reciprocating motion of the pushing or pivoting (tube) shaft 12 inside the instrument shaft 2. Furthermore, inside the pushing tube shaft 12 a rotating (tube) shaft 24 is supported such that the rotating (tube) shaft 24 is held rotatable and optionally axially shiftable relative to the pushing tube shaft 12. Alternatively, the rotating tube shaft 24 is just rotatably held in the pushing tube shaft 12 and comprises an axial bore in which an additional actuating rod 25 is shiftably supported.

A rotating motion of the knob 6 will be transmitted by a transmission inside the coupling member 8 (not shown) and converted into a rotating motion of the rotating tube shaft 24 inside the pushing tube shaft 12 wherein an operation of the trigger 7 will be transmitted by another transmission inside the coupling member 8 (not shown) into a shifting motion of the rotating tube shaft 24 (in case the rotating shaft gets two activating objects) or alternatively into a shifting motion of the actuating rod 25 inside the rotating tube shaft 24 as is shown in the figures. Such kind of transmission and handle is basically known in the art, for example according to the U.S. Pat. No. 7,674,255, so that reference to this document can be made, here.

Inside the rotating tube shaft 24 or, alternatively, inside the actuating rod 25 at least one, preferably two cable strands 33, 34 are fixedly located in an electrical isolated manner, which cable(s) 33, 34 serve for transmitting electric current to and for mechanically connecting the actuating rod 25 (or the rotating tube shaft 24) with the effector 3, especially, the surgical working tool built-in the effector 3, as will be described later.

The instrument head 4 is pivotally connected to the instrument shaft 2 via a hinge mechanism 17 comprising two eyelets 15 formed at the distal end portion of the instrument shaft 2 and defining a pivoting axis of the instrument head 4. Furthermore, the instrument head 4 consists of a cylindrical housing 16 at which two pins or bolts (not shown in the figures) are integrally formed which are co-axially aligned with each other such that they can be fitted into the eyelets 15 for forming a virtual pivoting shaft of the hinge 17. The pushing tube shaft 12 comprises at its distal end a connecting element in the form of an eyelet 14 at which a lever 19 is connected which lever 19 is pivotally connected to the housing 16 of the effector 3 at a connecting point 18. In case, the pushing tube shaft 12 is axially shifted inside the instrument shaft 2 this shifting motion is transferred to the housing 16 of the effector 3 via the intermediate lever 19 to pivot the effector 3 (which means, the instrument head 4) around the pivoting axis of the hinge 17.

As already stated above, inside the pushing tube shaft 12 the rotating tube shaft 24 is supported having a distal end, at which a bending flexible, torsional rigid, hollow spindle 30 is mounted. This spindle 30 according to FIG. 4 consists of a spiral spring each coil thereof preferably having a rectangular cross-section. Alternatively, the cross-section could also be trapezoidal or triangular. The inner diameter Di of the spring is min. 0.3 mm and the outer diameter of the spring is max. 5.5 mm. Therefore, the spring meets the form $$V=Da/Di<=18.33 \text{ with } Di>0 \text{ and } Da<=5.5 \text{ mm}. \quad (1)$$

Figure 4:
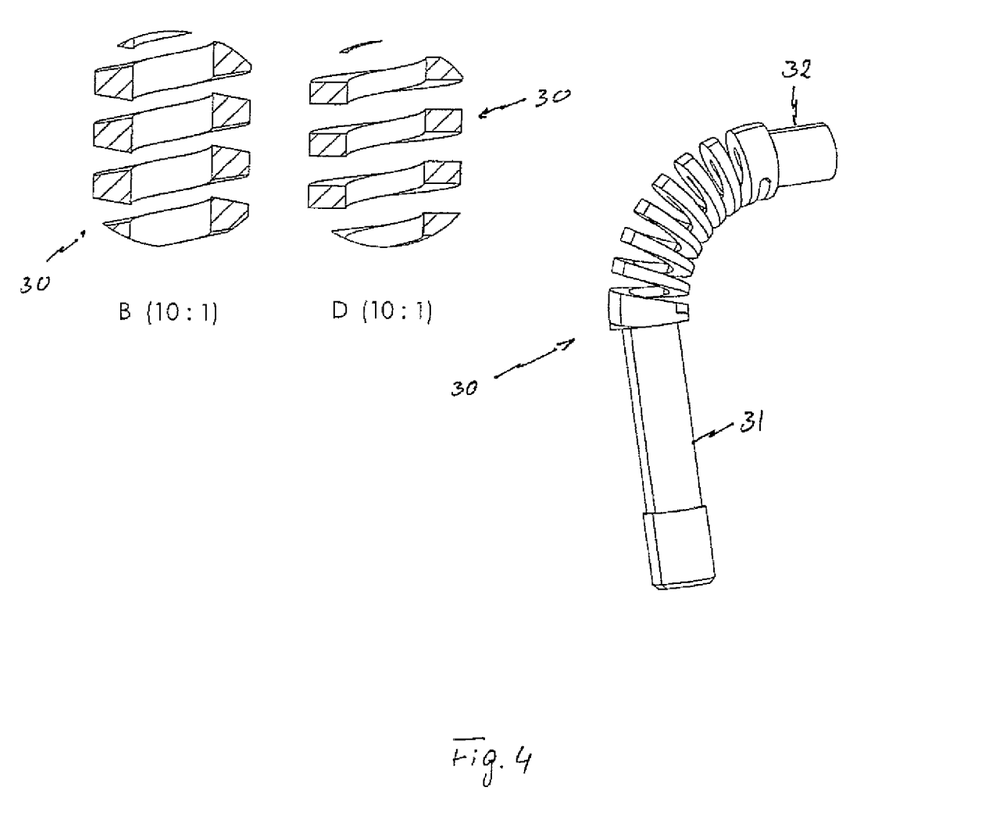
FIG. 4 shows a flexible spindle preferably in the form of a spiral spring.
Figure 5:
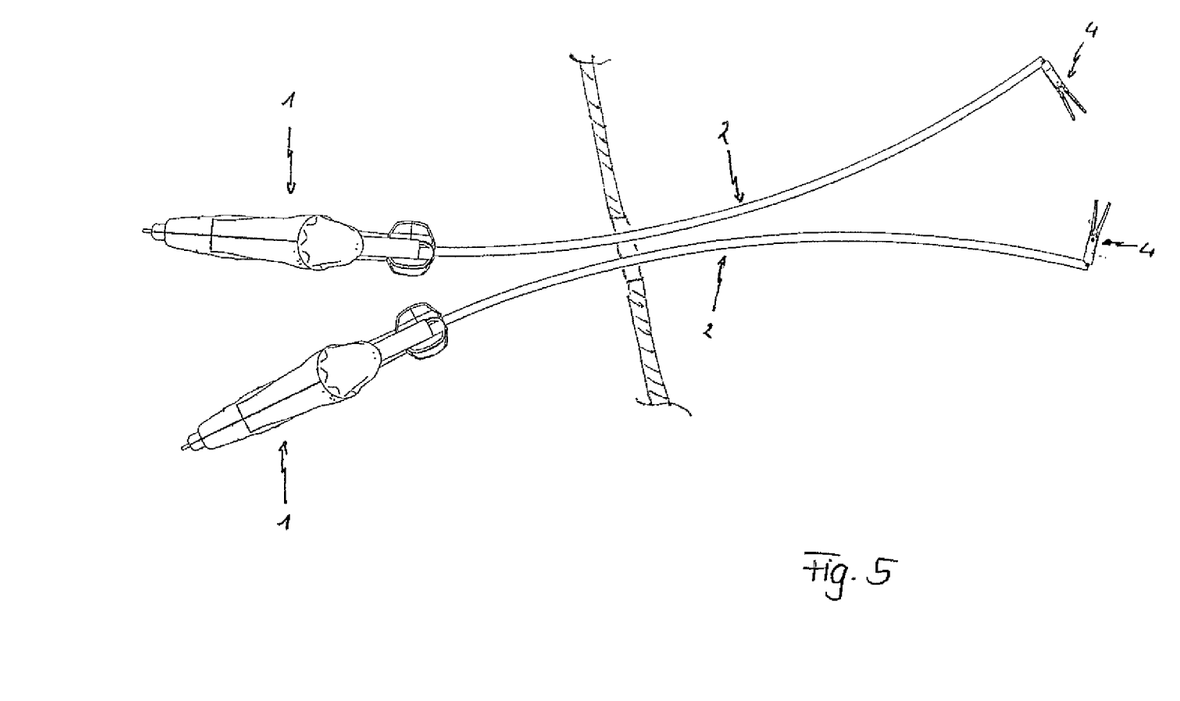
FIG. 5 shows the arrangement of two instruments in case of single port surgery.

The spring is made of a single block of spring steel having up to 9 coils (within the actively bent portion) and two integrated connecting elements 31, 32 at its longitudinal end portions. As already stated before the tensile strength Rm of the spring material shall preferably be $Rm>=1100 \text{ N/mm}^2$.

The one connecting element 31 of the spiral spring 30 is connected with the rotating tube shaft 24 to be able to transfer a torque. In the first alternative case of two functions for the rotating tube shaft 24 (rotating and opening/closing function of the effector 3) the connecting element 31 has to be shiftable versus the rotating tube shaft 24 into the longitudinal direction. In the second alternative case, the separate (additional) actuating rod 25 is arranged inside the rotating tube shaft 24 wherein the rotating tube shaft 24 takes only one function for rotating the effector 3 and the actuating rod 25 takes the other function to open/close the surgical working tool. Here, the one connecting element 31 can be a fixing means for fixing the flexible spindle 30 (spiral spring) to the distal end of the rotating tube shaft 24.

The opposite connecting element 32 is (in both alternative cases) fixedly connected with the effector 3 to transmit the rotating motion from the rotating tube shaft 24 to the effector 3. Inside the spring 30 at least one cable, preferably two cables 33, 34 are placed for which a resin tube (not shown) is inserted into the spring 30 (flexible spindle) which tube serves to guide the cable(s) 33, 34 in an isolated manner in accordance with a Bowden cable technique. The cable(s) 33, 34 is/are connected to the surgical working tool for its activation (opening/closing motion). Herefore, the working tool is preferably in the form of a forceps or a scissors means comprising two jaws, respectively, wherein at least one of them is pivotably supported by said effector 3 (its housing 16) and linked to the actuating rod 25 (or alternatively to the rotating tube shaft 24) via a lever means (not shown) and one of cables 33, 34 connected thereto such that an axial shift of the actuating rod 25 (or rotating tube shaft 24) caused by respective operating signals at the instrument handle 1 will be transmitted via the at least one cable 33, 34 and the lever means to the at least one jaw for its pivoting motion.

More concrete, the at least one or two cables 33, 34 is/are electrically and mechanically connected to at least one or the two jaws of the working tool which jaw(s) are electrically isolated. When axially shifting the actuating rod 25 (or the rotating tube shaft 24) the shifting movement thereof is transmitted via the cable(s) 33, 34 guided inside the flexible spindle 30 to the jaw(s) for pivoting motion. Additionally, an electric current can be applied to the jaw(s) via the cable(s) 33, 34 to create a heated point or just heat between the jaws which heat can be used to treat surgeries of a patient's body, for example to stop an inner hemorrhage.

The function of the above-described surgical instrument according to the preferred embodiment of the invention is as follows:

It is preferable, to use a single port surgery technology for inserting surgical instruments into a patient's body, in this case, via a single port trocar. In order to avoid negative influences of the instruments and to achieve a suitable distance between the distal tip portions of the instruments without crossing their instrument shafts inside the trocar, it is advantageous, to bent the instrument shaft 2, as it is shown in FIG. 1, substantially in a single C-shape or C-shape-like form as an alternative embodiment such that also the handles or interfaces for a robotic connection (not shown) on the proximal ends of each instrument are distanced from each other also in case, two or more instruments are inserted into a single trocar.

When actuating the handle 1 or the robotic interface for pivoting the instrument head 4, the pushing tube shaft 12 will be shifted axially inside the instrument shaft 2 wherein the shifting movement is transferred to the instrument head 4 via the lever 19 to pivot the instrument head 4 around the hinge 17. Here, a pivoting angle of at least 90° is achievable. The pivoting movement of the instrument head 4 also results in a bending movement of the spiral spring 30 directly interconnecting the effector 3 (located inside the housing 16 of the instrument head 4) with the rotating tube shaft 24 (located inside the pushing tube shaft 12) by bypassing the hinge 17 (traversing the virtual hinge shaft). Since the spiral spring 30 has coils the pitch thereof is defined in order to avoid any contact among the coils even in a max. bending position of the instrument head 4 (or, alternatively, the coils are allowed to get into touch with each other just at the max. pivoting position) the spiral spring 30 is able to transmit maximum torque with a minimum of outer dimension even in a maximum pivoting position of the instrument head 4. Therefore, the outer size of the spring can be maximally minimized.

When actuating the handle 1 for rotating the effector 3 inside the instrument head 4 (its housing 16) the rotating tube shaft 24 will be rotated within the pushing (pivoting) tube shaft 12 wherein this rotating motion is transmitted to the effector 3 via the spiral spring 30 independent from the pivoting position of the instrument head 4.

In the one alternative case of an arrangement of the additional actuating rod 25, the at least one cable or cables 33, 34 are located inside the actuating rod 25 which will follow the rotating movement of the rotating tube shaft 24. In the other alternative case according to which the rotating tube shaft 24 also takes the function of the actuating rod 25, which means, the additional actuating rod 25 is omitted, the at least one cable or cables 33, 34 are fixed within the rotating tube shaft 24 such that they will accurately follow the rotating motion of the rotating tube shaft 24 and the spiral spring 30 to maintain their relative position.

When actuating the handle 1 for opening/closing the forceps or a scissors means as being the surgical working tool of the effector 3, the actuating rod 25 will be shifted axially and relative to the rotating tube shaft 24 and the pushing tube shaft 12 wherein the axial movement will not be transferred to the spiral spring 30. In case of the alternative design, according to which the additional actuating rod 25 is omitted, the rotating tube shaft 24 will be axially shifted inside the pushing tube shaft 12 without shifting the spiral spring (flexible spindle) 30 because in this case its one connecting element 31 is designed to transmit just torque but not to transmit shear forces to the spiral spring 30. For example, the one connecting element 31 is shiftably supported within the rotating tube shaft 24 and has a cross-sectional profile allowing the transmission of rotational moments.

Therefore, in both alternative designs the axial movement of the actuating rod 25 or of the rotating tube shaft 24 is exclusively transferred to the forceps or a scissors means (especially the jaws thereof) via the at least one or two cables 33, 34 fixedly connected to the actuating rod 25 or the rotating tube shaft 24 and the jaw(s) and guided inside (by) the spiral spring 30 (or flexible spindle) according to a Bowden cable. For that reason, the forceps or a scissors means is actuateable (can be opened and/or closed) independent from the pivoting position of the instrument head 4 and independent from the rotating position of the effector 3 inside the instrument head 4.

Finally, when actuating the handle 1 for heating tissue via the jaws, electric current is applied to the jaws via the cables 33, 34 according to the so-called bipolar (HF) technology. Herefore, the jaws are pivotably held in an electric isolated manner by the effector 3, for example by using a resin material for the effector casing or by covering the jaws (and/or effector 3) with an isolation coating.

As can be gathered from the above description of the preferred embodiment of the invention a plurality of alternatives are possible which shall be covered by the enclosed patent claims:

Instead of the cited forceps or a scissors means a grasper, needle holder, Maryland dissector, etc. can be used as the surgical tool applied to the effector 3. Also a non-mechanically driven/actuated effector (working tool) can be used for the instrument, wherein in such a case, the at least one cable just serves for feeding electric current to that tool.

The preferred embodiment uses the bipolar HF technology, wherein, however, only one cable could be used for mechanical activation of the surgical woring tool. Here, to achieve bipolar technology the other cable could be exchanged for example by the instrument shaft and the effector casing itself, which have to be covered by an isolation coating.

According to the above description the tip deflection (pivoting the instrument head 4) is effected by the pushing tube shaft 12 in which the rotating tube shaft 24 and optionally the actuating rod 25 is supported. However, it is also possible, to use flexible cables for example in the form of Bowden cables to transmit shear forces (pushing/pulling forces) from the handle 1 to the instrument head 4 for its pivoting movement.

The tube shafts and rods inside the instrument shaft can be stiff or can have a certain flexibility to flexibly (elastically) follow the C-shape of the instrument shaft.

What is claimed is:

1. A surgical instrument comprising:
a mechanical signal generator in the form of an instrument handle or a robotic interface,
an instrument shaft having a distal end and a proximal end at which the signal generator is connected,
an instrument head, pivotally linked to the distal end of the instrument shaft via a hinge, and comprising an effector rotatably supported in said instrument head around a longitudinal axis of the instrument shaft, said effector holding at least one surgical tool in the form of a forceps or a scissors, and
a mechanical transmission system transmitting and/or converting mechanical operation signals from said signal generator to said instrument head, said mechanical transmission system comprising:
  a pushing tube shaft shiftably supported within said instrument shaft to transmit pivoting signals to said instrument head via a lever,
  a rotating tube shaft rotatably supported within said pushing tube shaft to transmit rotating signals to said effector via a bending flexible as well as torsional rigid, hollow spindle, and an actuating rod shiftably supported within said rotating tube shaft to transmit actuating signals from said signal generator to said surgical tool via a Bowden cable system comprising at least one push-/pull cable being guided within a resin tube which is inserted into the bending flexible as well as torsional rigid, hollow spindle, said bending flexible as well as torsional rigid, hollow spindle being arranged to bypass said hinge such that a first portion of said spindle is located between said mechanical signal generator and a hinge axis of said hinge, and a second portion of said spindle is located between said hinge axis and said instrument head, said spindle directly connecting said effector with said rotatable tube shaft, wherein said bending flexible as well as torsional rigid, hollow spindle has a spiral spring with coils in an axially middle portion thereof and a connecting element in form of a bar on each axial end portion thereof, said two connecting elements being integral with the spiral spring to form one piece, one bar of said bending flexible as well as torsional rigid, hollow spindle being connected to the rotating tube shaft and another bar of said bending flexible as well as torsional rigid, hollow spindle being connected to the effector, wherein a pitch of said spiral spring is configured such that:

in an unbent position, the coils are spaced apart from each other, and in a maximally bent position in accordance with a maximum pivoting position of the instrument head, the coils remain spaced apart from each other, and further wherein said bending flexible as well as torsional rigid, hollow spindle is serially inserted into the mechanical transmission system such that torque generated by the signal generator is transmitted to the instrument head via said spiral spring when said rotating tube shaft rotates within said instrument shaft, and said spiral spring additionally bends when said instrument head pivots about said hinge axis.

2. A surgical instrument according to claim 1, wherein said at least one cable additionally provides an electrical conductor for selectively applying electric power to said surgical tool.

3. A surgical instrument according to claim 1, wherein said lever is located radially outside of said bending flexible as well as torsional rigid, hollow spindle.

4. A surgical instrument according to claim 3, wherein said lever is positioned relative to said bending flexible as well as torsional rigid, hollow spindle such that a pivoting angle of at least 90 degrees is achieved.

* * * * *